(12) United States Patent
Halalay et al.

(10) Patent No.: US 7,370,514 B2
(45) Date of Patent: May 13, 2008

(54) DETERMINING QUALITY OF LUBRICATING OILS IN USE

(75) Inventors: Ion C. Halalay, Grosse Pointe, MI (US); Eric West Schneider, Shelby Township, Macomb County, MI (US); Michael William Rogers, Warren, MI (US)

(73) Assignee: GM Global Technology Operations, Inc., Detroit, MI (US)

( * ) Notice: Subject to any disclaimer, the term of this patent is extended or adjusted under 35 U.S.C. 154(b) by 372 days.

(21) Appl. No.: 11/106,309

(22) Filed: Apr. 14, 2005

(65) Prior Publication Data

US 2006/0232267 A1 Oct. 19, 2006

(51) Int. Cl.
*G01N 33/26* (2006.01)

(52) U.S. Cl. ..................................... 73/53.05

(58) Field of Classification Search ................. 73/53.05
See application file for complete search history.

(56) References Cited

U.S. PATENT DOCUMENTS

| | | | |
|---|---|---|---|
| 6,810,717 B2* | 11/2004 | Heremans et al. | ......... 73/53.05 |
| 2003/0222656 A1* | 12/2003 | Phillips et al. | .............. 324/605 |
| 2005/0035755 A1* | 2/2005 | Schilowitz et al. | ...... 324/158.1 |
| 2005/0104607 A1* | 5/2005 | Byington et al. | ........... 324/693 |

* cited by examiner

*Primary Examiner*—Hezron Williams
*Assistant Examiner*—Paul M West (57) ABSTRACT

Resistivity $\rho$ values of a lubricating oil are repeatedly determined at a predetermined temperature (range) as it is in use in a working mechanism such as a vehicle engine. Such accumulated properties over operating time of the working lubricant can be plotted graphically to display a curve with, for example, a first portion where $d\rho/dt>0$, a maximum $\rho_{max}$ at a time $t_1$ where $d\rho/dt=0$, a second portion where $d\rho/dt<0$, a minimum $\rho_{min}$ at a time $t_2$ where $d\rho/dt$ again is zero, and a third portion where $d\rho/dt>0$. Furthermore, there can exist another time $t_3$, where $d\rho/dt$ exhibits a discontinuous change (increase) with time. Characteristics of the $\rho$ vs. t curve, including, the values of $t_1$, $t_2$, $t_3$, $\rho_{max}$, $\rho_{min}$, and the ratio $\rho_{max}/\rho_{min}$ can be compared with like data on like lubricant oils in estimating the remaining useful life of the present operating lubricant oil.

21 Claims, 4 Drawing Sheets

FUNCTIONAL BLOCK DIAGRAM OF IMPEDANCE SENSOR ELECTRONICS

DETERMINING QUALITY OF LUBRICATING OILS IN USE

TECHNICAL FIELD

This invention pertains to determining the quality of lubricating oils used in engines, machines, or other lubricated mechanisms. More specifically, this invention pertains to the use of electrical measurements to estimate the quality (for example, the remaining useful life) of such a lubricating material in its operating environment.

BACKGROUND OF THE INVENTION

Oils are used as lubrication fluids in engines for land vehicles, marine and air transportation, electric power generation and other internal combustion engine applications. Oils are also used to lubricate sliding contact surfaces in machines, and they are used as heat transfer fluids in various equipment applications. In many of these engine and machine applications, the oil is heated well above ambient temperatures in an oxidizing environment and subjected to high shear stresses which chemically degrade the oil. The oil may also be subjected to contamination from combustion or other external sources. Thus, the initial composition of the oil, that provided its specified lubricating properties, is gradually altered and its lubricating characteristics degraded.

One group of lubricants includes petroleum oils which are widely used in large volumes as lubricants in automotive engines and a wide range of other engines. Such petroleum oils, produced as refined distillation products of crude petroleum, generally range from low viscosity, with molecular weights as low as 250, to very viscous lubricants, with molecular weights up to about 1000. The physical properties and performance characteristics of such engine lubricants depend on the relative distribution of parafinic, aromatic, and alicyclic (naphthenic) components. Depending upon the engine application, these refined oils are formulated to contain special additives such as oxidation inhibitors, rust inhibitors, anti-wear and extreme pressure agents, friction modifiers, detergents, pour-point depressants, viscosity-index improvers, foam inhibitors, and dispersants for contaminants. Commercial engine oils are formulated to contain representatives of most or all of these classes of additives. Apart from petroleum-based or mineral-based lubricants, synthetic molecular carbon-containing and/or silicon-containing lubricant oils have been developed for automotive applications and other machine or mechanism lubricant requiring applications.

The development of lubrication oils is a sophisticated technology, but techniques for determining when lubricating oil, in use in an engine or other mechanism, has reached the end of its useful life are not so advanced. Typically, a fixed operating mileage, time, or an algorithm based on engine operating conditions is used as an indication that the oil is approaching the end of its useful life and should be changed. These indicators are usually specified to underestimate the remaining life of the oil so as to avoid damage to the engine or other mechanism. There is a need for a more accurate method for determining the remaining useful life of lubrication oil in a mechanism. Such a method would enable the useful life of the lubricant to be utilized without discarding the material too soon, and would avoid using the fluid too long to the detriment of the host machine or engine.

SUMMARY OF THE INVENTION

The practice of this invention will be illustrated in the context of operating automotive vehicle engines such as gasoline fueled, internal combustion engines. However, it will be apparent that the invention can be used in assessing the remaining useful life of high resistivity lubricant oils operating in virtually any engine or mechanism.

In a representative automobile engine, a petroleum oil (mineral-based) is pumped from a sump in the crankcase and sprayed and circulated around and over rotating and reciprocating members of the engine. The oil is heated by the engine to temperatures in the range of, for example, about 50° C. to about 150° C. and exposed to an oxidizing atmosphere. From time to time, during engine operation, a small representative portion of the circulating oil is diverted through a suitable compact impedance sensor located conveniently in oil passages, the oil pan, or any other suitable location on or near the engine. The sensor is arranged and constructed to permit oil to flow through it in one or more relatively thin film streams for determination of the present-time resistivity of the fluid. A record (history) of resistivity $\rho$ values of the working oil are obtained during operation of the engine. Permittivity $\epsilon$ values are readily obtained at the same time and may also be used in predicting remaining oil life.

When data concerning the properties of the oil are required, the sensor is powered by a suitable AC frequency generator. The input voltage to the sensor creates a time-varying electric field inside the fluid under test. The output current and phase angle between the output current and applied voltage are sensed and this data, together with the value of the input voltage is directed to a local microprocessor, which in automotive applications may be the engine's control module. The voltage, current and phase-angle signals are then used to calculate the impedance amplitude, the resistance and the reactance of the sensor-oil combination, and these values are used in turn for determining the electrical resistivity and, optionally, additionally the permittivity of the oil passing through the sensor. The oil property data (resistivity $\rho$ and permittivity $\epsilon$) is stored in the on-vehicle (or on-engine or on-machine) microprocessor for subsequent processing and analysis. The oil temperature is also recorded at the time when the electrical property data is obtained.

The resistivity $\rho$ of an oil is proportional to the drag force experienced by free charge carriers (free ions) moving through the medium under the influence of the applied electric field, and therefore to the viscosity $\eta$ of the medium, and inversely proportional to the number density of free charge carriers (ions) $N_i$, or $\rho \sim \eta/N_i$. Therefore, under circumstances in which the number of free charge carriers is constant (i.e. in the absence of chemical reactions that release free ions), the resistivity represents a measure of the fluid viscosity. The permittivity is a measure of the reorientation of molecular dipoles in the lubricant under the influence of an applied electric field. The permittivity of the oil will change when the dipole moments d of its microscopic constituents change, e.g. through chemical reactions (that incorporate oxygen or nitrogen atoms, or chemical moieties that contain oxygen or nitrogen atoms, into the molecular constituents of the oil) or though the addition of polar liquids such a water, ethanol or glycols to the oil. Besides being subjected to the applied electric field, dipoles inside a fluid are also subjected to thermal motion. While the electric field tends to align the dipoles in a direction parallel and opposite to the electric field, thermal motion tends to destroy this alignment and randomize dipole orientations through molecular collisions. Furthermore, viscous forces will tend to slow down the rotation of the dipoles in the electric field, as well as slow down the randomizing effect of thermal motion on their alignment, so the permittivity will also depend on the viscosity of the medium. Therefore, one has the proportionality $\epsilon \sim \eta\, N_d$, with $N_d$ being the number density of dipoles inside the medium. It is to be understood that the previous proportionalities relating lubricant viscosity to its resistivity and permittivity are derived for the heuristic purpose of data interpretation, and that the derivation of exact relationships for the electrical resistivity and permittivity of a fluid necessitate the use of statistical mechanics at a higher level of complexity.

Changes in the resistivity of the oil as a function of engine operation time reflect physical and chemical changes in the oil, and its time dependence has signatures indicative of oil quality. Various features of these signatures are used to determine the quality of the lubrication oil, as well as to predict its time to failure. The method is preferably practiced using a compact impedance-response sensor which is mounted in any suitable location in the lubrication system, and a control/interpretation algorithm which could be implemented as a stand alone device, or incorporated into preexisting computers on the engine or other lubricated device. The invention is suitable for use on automobiles, but also other engine powered devices (e.g. boat, trains, generators, etc.), and has potential application in any system that handles oil-like substances (oil used as a heat transfer fluid, for example).

The engine oil is intended to be used over, for example, a period of months or years depending upon the frequency and severity of vehicle engine operation. Accordingly, oil resistivity data is thus accumulated intermittently, for example, after each several hours of engine operation, to record a history of these oil properties. Preferably, this oil property data is obtained at substantially the same temperature (or within a narrow temperature range), selected in the range of normal oil usage conditions that obtain irrespective of weather or climate conditions.

When viewed graphically, as oil resistivity, $\rho$, in megaohm centimeter M$\Omega$·cm (y-axis) vs. accumulated test time t in hours (x-axis), the accumulating resistivity data stored in the microprocessor reveals a curve with characteristics that are useful in estimating the remaining useful life of the oil operating in the engine or machine. For example, in the case of typical passenger car motor oils, resistivity values steadily increase, over accumulated operating hours ($d\rho/dt>0$), from an initial value for new oil to a maximum value (at $t_1$ when $d\rho/dt=0$). This may be considered Region I. With additional operating hours, the resistivity values of the oil steadily decrease ($d\rho/dt$ now $<0$) to a minimum value (at $t_2$ with $d\rho/dt$ again 0) (Region II). Thereafter, with further operating time, the resistivity values continue to steadily increase until the useful life of the oil has been depleted at (Region III). The end of useful lubricant life is signaled by a very rapid increase in resistivity values with time at $t_3$ (Region 4). This "knee" can be identified by the very sharp increase in the value of the time derivative of the resistivity: $(d\rho/dt)_{t<t3}<<(d\rho/dt)_{t>t3}$.

Thus, accumulated $\rho$ vs. time data, viewed as a continuous linear curve, displays three consecutive slope ($d\rho/dt$) changes. The curve also displays two local extrema (maximum and minimum, where $d\rho/dt=0$) at specific times during oil usage, as well as a "knee" which is characterized by a sudden increase in the slope $d\rho/dt$. These times of maxima and minima $\rho$ values, the time of observance of the knee, and the $\rho$ values themselves including the ratio $\rho_{max}/\rho_{min}$, are useable both as an indicator of oil quality and as a predictor of the time to failure for an oil inside an engine.

Other objects and advantages of the invention will become apparent from a description of a preferred embodiment which follows.

DESCRIPTION OF PREFERRED EMBODIMENTS

This invention is a method for determining the quality and useful life of an engine lubrication oil. The method uses a suitable lubricating oil flow-through electrical impedance sensor for monitoring electrical properties of the oil in use in an engine or other operating mechanism. And the practice of the method is supported by suitable electronic instrumentation.

The Method.

It is difficult to make a priori predictions regarding the time dependences for the permittivity and electrical conductivity of engine oils, since they are complex fluids involving a mixture of numerous molecular compounds and one factor or another can prevail over all others during a limited period from the operating lifetime of an engine oil, with the balance changing with oil usage. However, a few general trends may be predicted, based on the general usage conditions of the oil and from the known behavior of the oil viscosity during its useful lifetime, barring the overriding influence of other yet-to-be-determined factors. The viscosity of the oil increases steadily during most of its useful lifetime in the engine, except for a short period of time (up to 10-15 hours) at the beginning of its lifetime when it may decrease due to shear thinning. The increase in viscosity accelerates at the end of the useful lifetime of the oil, past a break in the slope $d\rho/dt$ of its time dependence. There exists, therefore, the expectation of generally increasing trends over time for both the resistivity and the permittivity. Engine oils, like all hydrocarbons, are rather nonpolar dielectric liquids, with electrical permittivities ranging from 2 to 3. Increases in oil permittivity are to be expected throughout the life of the oil, since the combustion process will cause both oxidation and nitration of the molecular components of an engine oil, and also may introduce water into the engine oil. Resistivity values for the oil are expected to be very high (in the M$\Omega\cdot$cm to G$\Omega\cdot$cm range), unless particular usage conditions cause the accumulation of water from the combustion process, which will lower the resistivity though the introduction of charge carriers (protons) in the oil. The presence of water in the engine oil, even in small amounts, can lead to significant increases in its permittivity, since $\epsilon=80$ for water. Significant amounts of water in the engine oil could also lower the value of the measured resistivity, since the auto-ionization of water can release free charge carriers (protons) into the oil. As a consequence of these facts, the measurement conditions (measurement temperature and the exact moment of measurement during the engine operation cycle, i.e. start-up, steady-state operation, transients such as accelerations or deceleration, or, shut-down) must be chosen judiciously, in order to minimize the possibility of errors in diagnostics due to effects other than those associated with aging of the oil due to engine operation.

Figure 1:
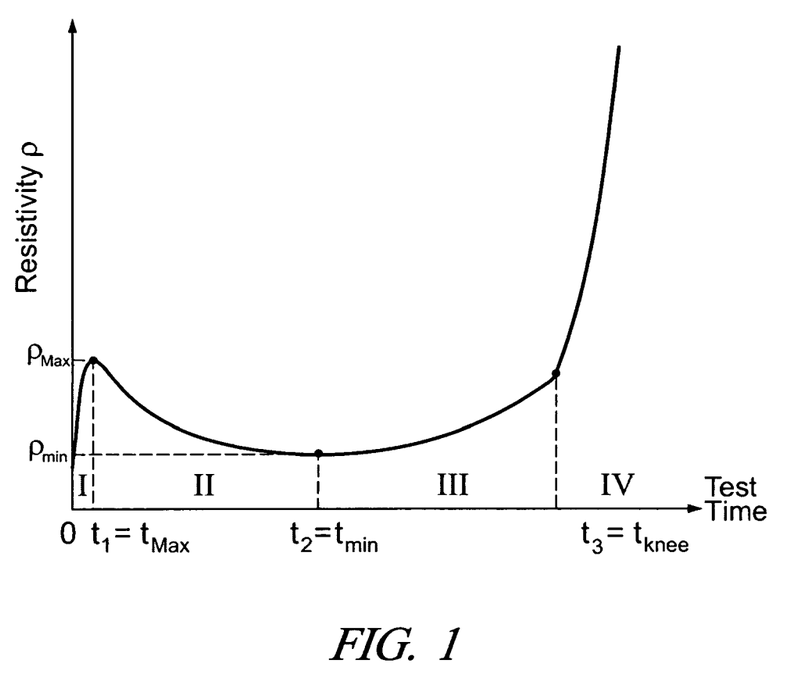
FIG. 1 is a graph of electrical resistivity $\rho$ vs. test time t for a representative engine oil in a spark ignition engine operated under steady state conditions.
Figure 2:
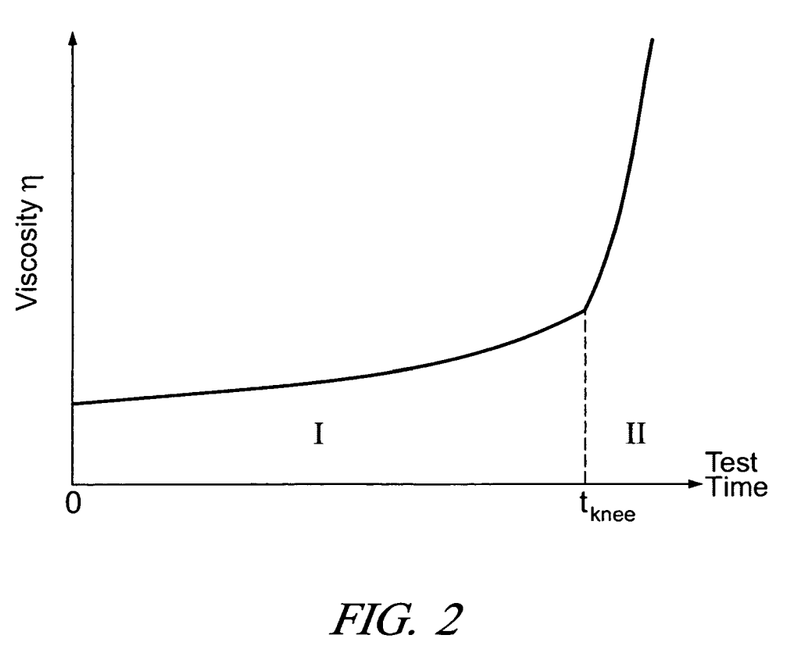
FIG. 2 is a graph of viscosity $\eta$ vs. test time t for the engine oil of FIG. 1 in an engine operated under steady state conditions.

Examples of the time dependences of the electrical resistivity and viscosity of an oil, while an engine is operating under steady state conditions, are shown in FIGS. 1 and 2, respectively. When viewed graphically, as oil resistivity $\rho$, in mega-ohm centimeter M$\Omega\cdot$cm (y-axis) vs. accumulated test time t in hours (x-axis), the accumulating resistivity data stored in the microprocessor reveals a curve with characteristics that are useful in estimating the remaining useful life of the oil operating in the engine or machine. As can be seen from FIG. 1, there exist four distinct regions in the time dependence of the resistivity. In Region I (where $d\rho/dt>0$) resistivity values increase steadily over accumulated operating hours, from an initial value for new oil to a maximum value $\rho_{Max}$ (when $d\rho/dt=0$) at time $t_1$ or $t_{Max}$. In Region II, the resistivity values of the oil steadily decrease with additional operating hours ($d\rho/dt<0$ now), until they reach, a minimum value $\rho_{min}$ (with $d\rho/dt$ again equal to 0), at time $t_2$ or $t_{min}$. Thereafter, in Region III, the resistivity values continue to steadily increase with further operating time, until the useful life of the oil has been depleted. This is signaled by a "knee" in the time dependence of the resistivity at time $t_3$ ($t_{knee}$) that signals the start of Region IV, which is characterized by a very rapid increase in resistivity values. This "knee" can be identified by a sudden increase (in some cases almost a discontinuous "jump") in the value of the time derivative of the resistivity: $(d\rho/dt)_{t<t3} << (d\rho/dt)_{t>t3}$.

Thus, accumulated $\rho$ vs. time data, viewed as a continuous linear curve, displays three consecutive changes in the sign of the slope $d\rho/dt$. The curve also displays two local extrema (maximum and minimum, where $d\rho/dt=0$) at specific times during oil usage, as well as a "knee," which is characterized by a sudden increase in the slope $d\rho/dt$.

In contrast, the viscosity exhibits only a monotonic change over the same time interval, as shown in FIG. 2, with no features that distinguish between the time intervals corresponding to the regions I, II and III in the time dependence of the electrical resistivity. There exists, however, a "knee" in the time dependence of the viscosity, at the same moment $t_{knee}$ as that for the drastic change in the time dependence of the resistivity. Region I of FIG. 2 shows steadily increasing viscosity of the oil until the oil usage or test time reaches $t_{knee}$. The steep increase in viscosity occurring at times (Region II of FIG. 2) greater than $t_{knee}$ signals the end of the useful life of the oil. Oil analysis data (and, in particular, the viscosity) exhibit no dramatic changes during the engine operating times corresponding to regions I, II and III of FIG. 1. However, the viscosity exhibits a drastic increase in region IV (see FIG. 2) signaling imminent engine failure due to improper lubrication.

Figure 3:
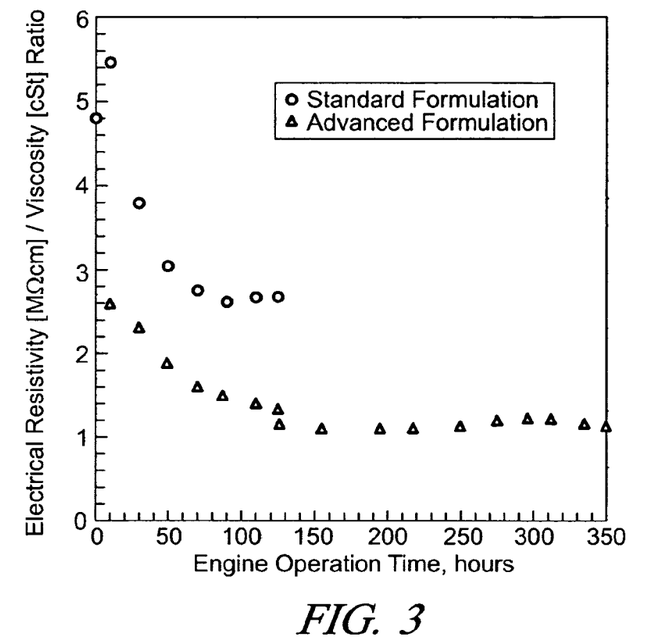
FIG. 3 is a graph of the ratio of electrical resistivity [M$\Omega$·cm] to viscosity [cSt] vs. test time in hours for a standard mineral-based engine oil, S, (open circle data points) and an advanced synthetic engine oil, A, (open triangle data points)

While some (but not all) conventional methods of oil analysis are capable of detecting the end of the useful life of an engine oil, the moments of time corresponding to the maximum and minimum in the time dependence of resistivity values $\rho$, as well as the $\rho$ values themselves, are useable both as an indicator of oil quality and as a predictor of the time to failure for an oil inside an engine. Furthermore, the "knee" at $t_3$ in the time dependence of the electrical resistivity, serves as an end-of-life indicator for the engine oil, as the moment of its occurrence coincides with the moment marking the start of a drastic increase in engine oil viscosity. Regions I and II (referring to FIG. 1) in the time dependence of the electrical resistivity reveal the existence of two (possibly related) chemical processes, occurring on two markedly different time scales. The time dependence of the electrical resistivity in Region I is dominated by a fast chemical process (with a characteristic time scale ranging from 1 to 20 hours in the present examples), that depletes charge carriers, while the time dependence in Region II is dominated by a slow chemical process (with a characteristic time scale ranging from 40 to 150 hours in the present examples), that releases free charge carriers into the oil. Note that the increase in the resistivity occurring in Regions III and IV is solely due to the increase in viscosity, as demonstrated by FIG. 3, which displays the ratio between the electrical resistivity and the viscosity, for two oils of varying quality. The said ratio is almost constant at times corresponding to Regions III and IV, which indicates that all chemical processes that release free ions into the oil have ceased to any appreciable extent by the time the minimum in the electrical resistivity has been reached at time $t_2$.

The above findings represent the underpinning of this method for determining the useful life of lubricating oils for an internal combustion engine, which leads to the algorithm described below.

(1) Measure the sensor impedance Z (f, t, T)=Z' (f, t, T)+iZ" (f, t, T) at one or more frequencies separated by decade steps at a known temperature, as a function of time (2) Determine the resistivity $\rho$ of the oil and construct its time history.

(3) Estimate the useful life of the oil from the derivatives $d\rho/dt$:

I. If at the measurement time t', one has $$\left(\frac{d\rho}{dt}\right)_{t=t'} = 0$$

and $$\left(\frac{d\rho}{dt}\right)_{t<t'} > 0,$$

then $t_M=t'$; use $t_M$ to obtain a first estimate for the time-to-failure of the oil.

II. If at the measurement time t", one has $$\left(\frac{d\rho}{dt}\right)_{t=t''} = 0$$

and $$\left(\frac{d\rho}{dt}\right)_{t<t''} < 0,$$

then $t_m=t''$; use now both $t_M$ and $t_m$ to obtain an improved estimate for the time-to-failure of the oil. Additionally, or alternatively, the values $\rho_{max}$, $\rho_{min}$, and/or the ratio $\rho_{max}/\rho_{min}$ may also be compared with previous data to estimate time-to-failure.

Alternatively, one may choose to calculate the second time derivative $d^2\rho/dt^2$ as well, in order to discriminate between a maximum and a minimum, instead of using the inequalities $$\left(\frac{d\rho}{dt}\right)_{t<t'} > 0 \text{ and } \left(\frac{d\rho}{dt}\right)_{t<t''} < 0.$$

A third way to distinguish between a maximum and a minimum is to use the simple ordering relations $\rho(t')<\rho(t\neq t')$ and $\rho(t'')>\rho(t\neq t'')$ that obtain, respectively, in the vicinity of a maximum and a minimum.

(4) Trigger Change Oil indicator before predicted time to failure is reached.

(5) If oil has not been changed and the time derivative of the resistivity experiences a sudden increase at some time t''', $(d\rho/dt)_{t<t'''}<<(d\rho/dt)_{t>t'''}$ then issue a warning to the vehicle or machine operator.

Figure 4:
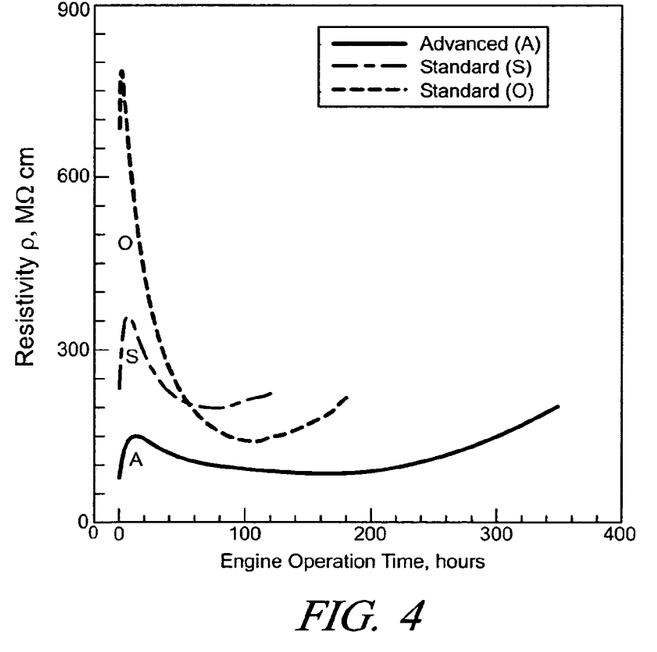
FIG. 4 is a graph of electrical resistivity $\rho$, M$\Omega$·cm vs. engine operation time, hours for an obsolete mineral-based engine oil, O, (upper curve), a standard mineral-based engine oil, S, (middle curve) and an advanced synthetic engine oil, A, (lower curve)

The capabilities of the present method are illustrated in FIG. 4 which displays respectively, the electrical resistivity and viscosity for three engine oils of varying quality. Each of these oils was of commercial origin and fully formulated with unspecified additives including an oxidation inhibitor, rust inhibitor, anti-wear and extreme pressure agent, friction modifier, detergent, pour-point depressant, viscosity-index improver, foam inhibitor, and dispersants for contaminants.

FIG. 4 is a graph of resistivity data for a previous generation mineral-based engine oil (O, bold dashed line), a standard oil (S, long dash-short dash line) and an advanced oil (A, solid line) versus test time in hours. Oil O, a mineral-based oil not presently specified for vehicle use, was tested to evaluate the method of this invention on a broader range of oil compositions. Standard oil S is a GF-3 mineral-based engine oil such as is used in the engines of new vehicles. The advanced oil A was wholly synthetic GF-3 oil of advanced formulation, such as might be used by some vehicle owners for engine-fill. The oil samples were used, respectively, in high temperature high load engine dynamometer tests, in which the test engine was operated at 3000 rpm under a constant load of 103 Nm. At the time that impedance data were taken the oil temperature at the sensor was 130° C.

A portion of the oil circulated through the engine by its oil pump was routed through an impedance sensor which is illustrated in cross-section FIG. 5 as will be described below. Electronic instrumentation was used to provide alternating current signals to the impedance sensor at selected times and at a known sensor temperature. The nature and function of the impedance sensor system electronics is illustrated and summarized in FIGS. 6 and 7. This instrumentation and associated microprocessor sensed the impedance of the flowing-oil-filled sensor and determined the resistivity $\rho$ in M$\Omega$·cm at regular time intervals of 15 minutes during the first 20 hours of testing and at time intervals of 30 minutes for the remainder of each test.

The data displayed in FIG. 4 represents a resistivity history $\rho(t)$ of the oils during actual engine operation. The initial resistivity value of oil O was 680 M$\Omega$·cm, of oil S was 231 M$\Omega$·cm, and of oil A was 77 M$\Omega$·cm. As dynamometer testing time progressed, each oil sample experienced a reduction in charge carrier density N and their respective resistivity values $\rho$ increased rapidly. After a relatively short time, the resistivity values for each oil sample reached maximum values: 780 M$\Omega$·cm at 1.5 test hours for oil O, 360 M$\Omega$·cm at 6 test hours for oil S, and 149 M$\Omega$·cm at 12 test hours for oil A. Thus, the first derivative of resistivity with time $(d\rho/dt)$ for these samples was initially >0. In each case resistivity then reached a maxima at $t=t_{Max}$ when the value of the slope is zero, $(d\rho/dt)=0$. The respective times for each oil to reach its maximum resistivity value was $t_{Max,O}=1.5$ hours, $t_{Max,S}=6$ hours, and $t_{Max,A}=12$ hours.

After reaching local maximum values of $\rho$, subsequent values of resistivity decreased monotonically with further testing time $(d\rho/dt<0)$ until at a time of $t=t_{min}$ specific to each oil sample, local minimum values of $\rho$ were detected, when the value of the slope is again zero, $(d\rho/dt)=0$. The low value of $\rho$ for oil O was 148 M$\Omega$·cm at $t_{min}=102$ hours, the low value of $\rho$ for oil S was 200 M$\Omega$·cm at $t_{min}=75$ hours, and the low value of $\rho$ for oil A was 86 M$\Omega$·cm at $t_{min}=148$ hours.

Testing reflected in FIG. 4 was stopped before either oil S or oil A experienced a failure as would be evidenced by an excessive increase in its viscosity. Oil O was tested for a period of time beyond the "danger point." However, the surprisingly similar and characteristic graphs represent signatures of the respective oils useful in predicting their remaining useful life or time to failure.

In order to provide reference data for oil life predictions, oil samples can be tested to failure to obtain detailed $d\rho/dt$ histories. Such histories can be stored in the memory of a microprocessor detecting and recording $d\rho/dt$ data for a presently working oil sample. While each oil sample (whether of identical or of functionally comparable composition) experiences different load and environmental conditions, the $d\rho/dt$ data are similar and can be compared for reliable predictions of remaining useful lubricating life. In this way lubricating oils can be used to their full capabilities without early and wasteful discarding of materials of limited availability.

An Impedance Sensor.

Figure 5:
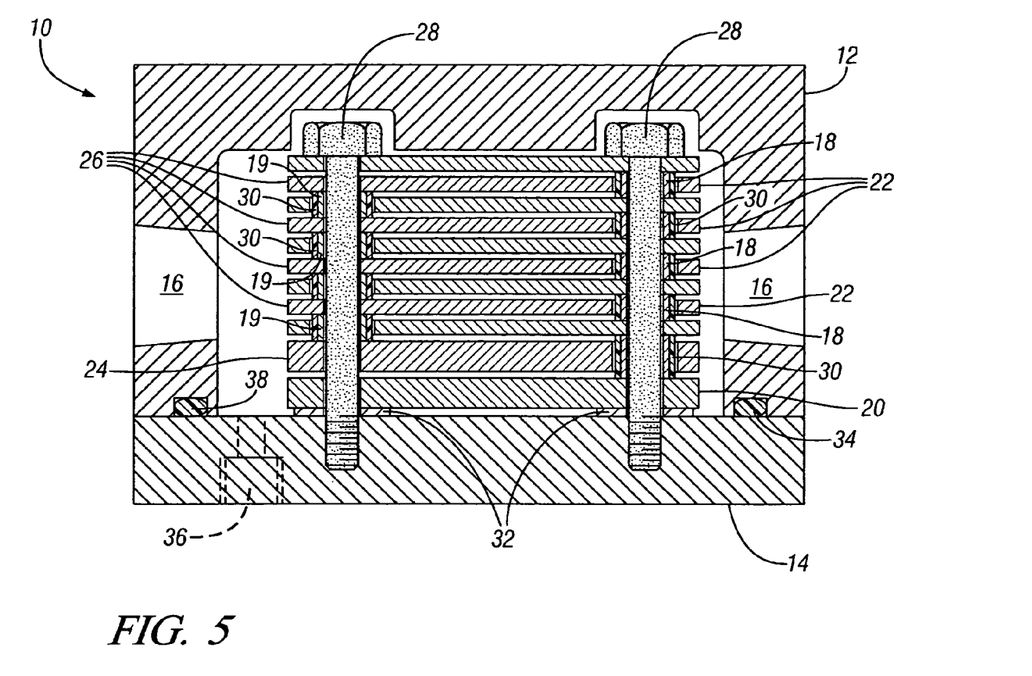
FIG. 5 is a side view in cross-section of a flow-through impedance sensor for determining electrical properties of a lubricating oil during, for example, engine operation in the practice of this invention.

FIG. 5 depicts a cross-sectional view of an impedance sensor preferred for use in the practice of this invention. The sensor shown in FIG. 5 can be located, for example, in the oil passages or the oil pan of an operating vehicle engine. During operation of the engine, lubricating oil is continually pumped from its sump in the oil pan around and over moving parts of the engine. Typically the temperature of the circulating oil is measured and reported to an engine control module (or powertrain control module, PCM) employed in controlling engine (and transmission) operation. In accordance with this invention, oil is caused to flow through a suitable sensor such as impedance sensor 10 illustrated in FIG. 5.

When located in oil passages, the sensor 10 requires a metallic enclosure that comprises an upper cell housing 12 and a lower cell mounting flange 14. Besides enabling the passage of oil through the sensor, the housing members 12, 14 also provide electrical shielding of the sensor from electrical interference that may be caused by ignition sparks. Cell housing 12 has oil flow ports 16. For vehicle engine applications these housing members may be made of a suitably castable or formable metal alloy, such as an aluminum alloy. No special enclosure is needed in cases where the sensor is placed inside the oil pan, as the pan itself can provide adequate electrical shielding.

Within cell housing 12 several stacked circular plates form an interleaved capacitor, with six sets of circumferentially and vertically spaced, metal contact tubes 18, 19 (one set of each of 18 and 19 shown in FIG. 5) placed perpendicular to, and supporting the plates. The sets of metal contact tubes 18, 19 provide electrical contacts between every other plate. The plates are spaced uniformly, about one millimeter apart. A first connecting plate 20 is connected to a first set of five alternate inner capacitor plates 22 through three sets (one set shown in FIG. 5) of five alternating contact tubes 18. A second connecting plate 24, overlying and spaced from first connector plate 20, is connected to a second set of four alternate inner capacitor plates 26 by means of the other three sets of four alternating contact tubes 19. Six circumferentially spaced, non-conductive, fastening bolts 28 (two shown in the cross-sectional view of FIG. 5) extending vertically through the vertical sets of contact tubes 18, 19 attach the capacitor assembly to cell mounting flange 14. Insulating layer 30 on the exterior surface of each contact tube 18 ensures that the electric field lines, and thus the electrical current flow, in the cell are perpendicular to the capacitor plates. Circular capacitor plates 20, 22, 24, and 26 are suitably made of stainless steel (or any other suitable metal or metallic alloy, such as nickel, Inconel, Hastelloy, etc.) and have a diameter of about 43 mm.

As stated and illustrated, the capacitor parts are held together, and mounted rigidly onto the cell mounting flange 14, by means of the six fastening bolts 28 which are made of rigid plastic material, in order to prevent shorting of the capacitor plates. Six insulating spacers 32 (two shown) between connecting plate 20 and mounting flange 14 also serve to prevent shorting between the cell capacitor plates 20, 22, 24, and 26 and mounting flange 14.

An O-ring 34 affects an air-tight seal between the cell housing 12 and the mounting flange 14. The liquid under test is introduced into, and removed from, the measurement fixture by means of two fluid ports 16. Both the cell housing 12 and the cell mounting flange 14 are made of metal and effect an electrical shielding of the measuring capacitor and are connected to electrical ground.

Electrical connections between the measuring capacitor and the measuring electronics are effected by means of two or, preferably, four coaxial cables (not shown) that enter the measurement fixture through the coaxial cables port 36 (lying behind the sectional surface shown in FIG. 5) of the cell mounting flange 14 into cell space 38 and have their inner conductors pair-wise connected to the two lower connecting plates 20 and 24. In the case of four coaxial cables, the inner conductors are pair-wise connected to the two connecting plates. The coaxial cables are sealed into the cell mounting flange by means of high-temperature insulating epoxy and their outer conductors are electrically connected to the cell housing.

The impedance sensor 10 is, of course, filled with the fluid under test, in order to determine the fluid's electrical properties. The sensor can operate both in batch mode (by filling the cell through one of the ports and then closing both ports with plugs) as well as flow-through mode (with the liquid under test flowing through it). The oil is usually at or near its operating temperature when it flows between the closely spaced capacitor plates. The oil-filled sensor is then connected to an impedance measuring instrument (LCR meter, auto-balancing ac bridge, frequency response analyzer, etc) and its electrical impedance is determined over some frequency range of interest. The electrical resistivity of the fluid can then be determined from the measured resistance and the cell constant, and the electrical permittivity of the fluid can be determined from the measured capacitance and the vacuum capacitance of the cell.

The sensor can be used to determine the electrical resistivity (or, equivalently, the electrical conductivity) and the electrical permittivity of any fluid of automotive interest (engine oils, transmission fluids, coolants used in engines or for machining, hydraulic fluids, battery electrolytes). It has been used for determining the properties of fresh and used engine oils. Furthermore, the sensor can be used for in-line monitoring of engine oils during high temperature dynamometers tests, without any significant deterioration in its performance after more than 1200 hours of testing at 130° C.

Electronic Circuit and Instrumentation for Oil Life Testing.

Figure 6:
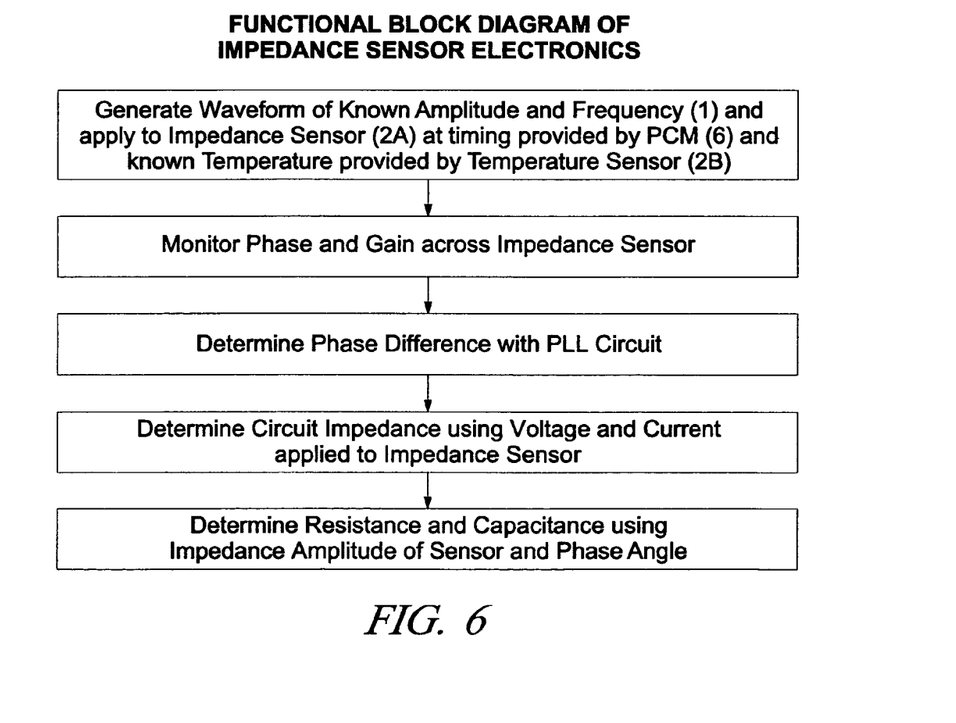
FIG. 6 is a functional block diagram of electronic instrument operations in connection with an impedance sensor for determining electrical properties of a lubricating oil during engine operation.
Figure 7:
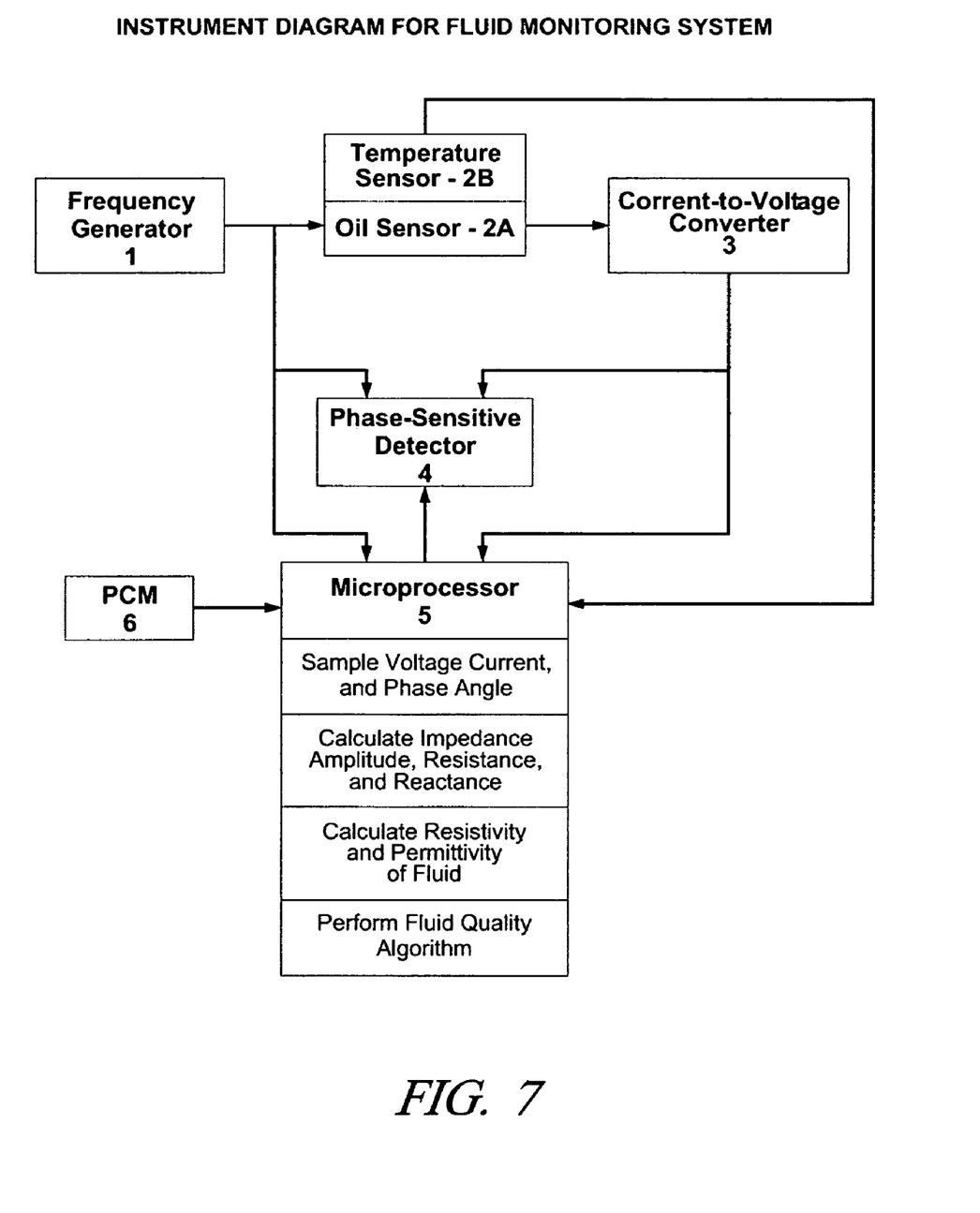
FIG. 7 is an instrument diagram for monitoring electrical properties of a lubricating oil during engine operation.

FIG. 6 illustrates, in flow diagram form, the functional steps for determining the resistivity and, optionally, additionally the permittivity of a lubricant oil in use. FIG. 7 is also a block flow diagram illustrating the relationship of electronic devices (instruments) for such a fluid monitoring system. These illustrations are in the context of an operating four-cycle, internal combustion engine.

Reference is made to the five process flow blocks of FIG. 6 starting with the first (top) block. When data concerning the properties of the oil are required, the sensor is powered by a suitable AC frequency generator (indicated at block 1 in FIG. 7) which generates a waveform of known amplitude and frequency. The frequency is suitably scanned downward from 100 MHz to 0.1 Hz, for example, with 3-20 data points per frequency decade. This input voltage to the oil property impedance sensor creates a time-varying electric field inside the fluid under test. The timing of the input voltage is provided by a powertrain control module (PCM) of the type used on modern vehicles to manage engine and transmission operation. The temperature of the oil in the sensor is also sensed and transmitted to the PCM or to an oil property microprocessor under the control of the PCM.

The output current and phase angle between the output current and applied voltage across the impedance sensor are sensed and this data, together with the value of the input voltage is directed to the PCM as indicated in block 2 of FIG. 6.

The PCM interacts with a phase lock loop circuit (PLL) to determine phase differences (block 3).

The voltage, current and phase-angle signals are then used to calculate the impedance amplitude, the resistance and the reactance of the sensor-oil combination (block 4). And these values are used in turn for determining the electrical resistivity and/or the permittivity of the oil passing through the sensor (block 5). The oil property data (resistivity $\rho$ and permittivity $\epsilon$) is stored in the PCM for subsequent processing and analysis.

FIG. 7 complements FIG. 6 by providing a suitable schematic flow diagram for the instruments, PCM, and dedicated microprocessor for determining oil quality.

Frequency generator 1 activates the oil impedance sensor 2A with AC signals of predetermined amplitude and frequency. The signals are also received by a phase sensitive detector 4 Dedicated microprocessor 5 samples voltage data from frequency generator 1 and data from phase sensitive detector 4. Microprocessor 5 is prompted by, or under control of, PCM 6. Concurrently, oil temperature data from oil temperature sensor 2B is provided to microprocessor 5.

Output current signals from sensor 2A are received by current-to-voltage converter 3. Voltage signals from converter 3 are sent to phase-sensitive detector 4 and current and phase angles data sampled by microprocessor 5 Microprocessor 5 calculates impedance amplitude, resistance and reactance of the sensor. Using the calculated data and stored constants pertaining to characteristics of the sensor 2A, the microprocessor 5 calculates current resistivity and permittivity values of the working oil. These values are stored in the dedicated microprocessor and used in an algorithm based on time-based resistivity data and/or time-based permittivity data as described in method section of this specification.

Resulting oil life data is transmitted form the microprocessor 5 to the PCM 6 which regularly apprises a vehicle operator of current oil condition.

The practice of the invention has been described by reference to certain examples which are provided for the purpose of illustration and not for limitation of the invention.

The invention claimed is:

1. A method of determining remaining useful life of a quantity of oil in use in fluid lubrication of an operating mechanism, the method comprising:
   repeatedly determining resistivity ($\rho$) values of the oil at an predetermined oil temperature during operating time intervals of the mechanism;
   recording a resistivity-time $\rho(t)$ history of the oil such that, as successive resistivity values starting with an initial value are accumulated with elapsed operating time, a continuous $\rho(t)$ linear curve is formulated that includes; (1) a first portion with a slope of $d\rho/dt>0$ up to a first time $t_1$ during which values of $\rho$ increase and (2) a maxima at $t_1$ where $d\rho/dt=0$ with a corresponding $\rho_{max}$;
   comparing, from time to time, the then existing portion of the $\rho(t)$ curve with like predetermined data on a like or functionally comparable oil composition;
   using the comparison to predict the remaining useful life of the oil;
   continuing to record a resistivity-time $\rho(t)$ history of the oil so that a continuous $\rho(t)$ linear curve is formulated that further includes; (3) a second portion with a slope of $d\rho/dt<0$ during which values of $\rho$ decrease up to a second time $t_2$, (4) a minima at $t_2$ where $d\rho/dt=0$ with a corresponding $\rho_{min}$, and (5) a third portion where $d\rho/dt>0$ ;
   continuing to compare, from time to time, the then existing portions of the $\rho(t)$ curve with like predetermined data on a like or functionally comparable oil composition and using the comparison to predict the remaining useful life of the oil;
   continuing to record a resistivity-time $\rho(t)$ history of the oil in the third portion of the $\rho(t)$ curve until time $t_3$ when there is a sudden increase in the value of the time derivative of the resistivity indicating that the useful life of the oil has been depleted; and then
   generating a signal indicating that the useful life of the oil has been depleted.

2. A method as recited in claim 1 in which the oil comprises a mineral-based oil derived from petroleum.

3. A method as recited in claim 1 in which the oil comprises a synthetic oil comprising carbon-based and/or silicon-based materials.

4. A method as recited in claim 1 in which the mechanism is a hydrocarbon fueled engine.

5. A method as recited in claim 1 in which the oil in the mechanism operates at temperatures above about 100° C.

6. A method as recited in claim 1 in which $t_2/t_1$ is about 10 or greater.

7. A method as recited in claim 1 in which $t_1$ is used to predict remaining useful life of the oil.

8. A method as recited in claim 1 in which $t_1$ and $t_2$ are used to predict the remaining useful life of the oil.

9. A method as recited in claim 1 in which $\rho_{max}$ is used to predict remaining useful life of the oil.

10. A method as recited in claim 1 in which $\rho_{min}$ and/or $\rho_{max}$ are used to predict remaining useful life of the oil.

11. A method as recited in claim 1 in which the ratio $\rho_{max}/\rho_{min}$ is used to predict remaining useful life of the oil.

12. A method as recited in claim 1 in which the oil is contained in an impedance sensor with a known resistivity constant, and the sensor is powered with an input voltage by an AC frequency generator in a time varying electric field at frequencies in the range of about 100 MHz to 0.1 Hz;
   the sensor output current and phase angle between the output current and input voltage are detected;
   the impedance amplitude, resistance and reactance of the sensor-oil combination are determined from the input voltage, output current and phase angle; and
   the electrical resistivity of the oil at the predetermined temperature is determined from the determined resistance and sensor resistivity constant.

13. A method of determining remaining useful life of a quantity of oil in use in fluid lubrication of an operating mechanism, the method comprising:
   repeatedly determining resistivity ($\rho$) values of the oil at a predetermined oil temperature under a time-varying electric field during operating time intervals of the mechanism;
   recording a resistivity-time $\rho(t)$ history of the oil such that, as successive resistivity values starting with an initial value are accumulated with elapsed operating time, a continuous $\rho(t)$ linear curve is formulated that includes; (1) a first portion with a slope of $d\rho/dt>0$ up to a first time $t_1$ during which values of $\rho$ increase, (2) a maxima at $t_1$ where $d\rho/dt=0$ with a corresponding $\rho_{max}$, (3) a second portion with a slope of $d\rho/dt<0$ during which values of $\rho$ decrease up to a second time $t_2$, (4) a minima at $t_2$ where $d\rho/dt=0$ with a corresponding $\rho_{min}$, and (5) a third portion where $d\rho/dt>0$ ;
   comparing, from time to time, the then existing portions of the $\rho(t)$ curve with like predetermined data on a like or functionally comparable oil composition;
   repeatedly using the comparison to predict the remaining useful life of the oil;
   continuing to record a resistivity-time $\rho(t)$ history of the oil in the third portion of the $\rho(t)$ curve until time $t_3$ when there is a sudden increase in the value of the time derivative of the resistivity indicating that the useful life of the oil has been depleted; and then generating a signal indicating that the useful life of the oil has been depleted.

14. A method as recited in claim 13 in which the oil is a mineral-based oil derived from petroleum.

15. A method as recited in claim 13 in which the oil is a synthetic oil comprising carbon-based and/or silicon-based materials.

16. A method as recited in claim 13 in which the mechanism is a hydrocarbon fueled engine.

17. A method as recited in claim 13 in which the oil in the mechanism operates at temperatures above about 100° C.

18. A method as recited in claim 13 in which $t_1$ and $t_2$ are used to predict the remaining useful life of the oil.

19. A method as recited in claim 13 in which $\rho_{min}$ and/or $\rho_{max}$ are used to predict remaining useful life of the oil.

20. A method as recited in claim 13 in which the ratio $\rho_{max}/\rho_{min}$ is used to predict remaining useful life of the oil.

21. A method as recited in claim 13 in which the oil is contained in an impedance sensor with a known resistivity constant, and the sensor is powered with an input voltage by an AC frequency generator in a time varying electric field at frequencies in the range of about 100 MHz to 0.1 Hz;

the sensor output current and phase angle between the output current and input voltage are detected;

the impedance amplitude, resistance and reactance of the sensor-oil combination are determined from the input voltage, output current and phase angle; and the electrical resistivity of the oil at the predetermined temperature is determined from the determined resistance and sensor resistivity constant.

* * * * *